United States Patent [19]

Murray et al.

[11] Patent Number: 4,871,669

[45] Date of Patent: Oct. 3, 1989

[54] PRODUCTION OF NATURAL FLAVOR ALDEHYDES FROM NATURAL SOURCE PRIMARY ALCOHOLS $C_2$-$C_7$

[75] Inventors: William D. Murray; Sheldon J. B. Duff, both of Ottawa; Patricia H. Lanthier, Wilson's Corners, all of Canada

[73] Assignee: Canadian Patents & Development Limited, Ottawa, Canada

[21] Appl. No.: 211,879

[22] Filed: Jun. 27, 1988

[51] Int. Cl.[4] .................... C12P 7/24; C12R 1/72; C12R 1/84; C12R 1/78

[52] U.S. Cl. .................... 435/147; 435/188; 435/921; 435/930; 435/938; 435/944

[58] Field of Search .............. 435/930, 147, 188, 921, 435/938, 944

[56] References Cited

U.S. PATENT DOCUMENTS

| | | | |
|---|---|---|---|
| 3,880,739 | 4/1975 | Leavitt | 435/147 |
| 4,250,261 | 2/1981 | Eggeling et al. | 435/147 |
| 4,481,292 | 11/1984 | Raymond | 435/147 |
| 4,503,153 | 3/1985 | Geigert et al. | 435/147 |
| 4,540,668 | 9/1985 | Hopkins | 435/190 |
| 4,619,898 | 10/1986 | Hopkins | 435/190 |

FOREIGN PATENT DOCUMENTS

| | | | |
|---|---|---|---|
| 0239005 | 9/1986 | German Democratic Rep. | 435/147 |
| WO87/04725 | 8/1987 | PCT Int'l Appl. | 435/147 |

*Primary Examiner*—Herbert J. Lilling
*Attorney, Agent, or Firm*—Alan A. Thomson

[57] ABSTRACT

Methylotrophic yeasts of the genera Pichia, Torulopsis, Candida and Hansenula when grown on methanol, make use of an enzyme, alcohol oxidase, to catalyse the initial oxidation of methanol to formaldehyde. Non-growing whole cells of such methylotrophic yeasts were used in place of purified alcohol oxidase for the production of flavoring aldehydes from their respective alcohols. To reduce end product inhibition a number of amine buffers, which chelate the aldehydes, were studied and an increase in aldehyde production was demonstrated with selected buffers which maintain a weakly alkaline pH.

20 Claims, 4 Drawing Sheets

LEGEND –
○ ETHANOL
● ACETALDEHYDE

PRODUCTION OF NATURAL FLAVOR ALDEHYDES FROM NATURAL SOURCE PRIMARY ALCOHOLS $C_2$-$C_7$

BACKGROUND AND PRIOR ART

This invention relates to a method for using non-growing, metabolically active methylotrophic yeasts to convert natural source primary alcohols to natural flavour aldehydes.

There is a consumer preference for natural products; such that food products labelled as containing "all natural flavours" have a market advantage over similar products containing artificial flavours. This preference has lead to a demand for natural flavours, but supply is limited. Accordingly, natural flavours command a much higher price than similar synthetic flavours.

Several factors tend to force the product price higher. Nearly all natural flavours are obtained as extracts from botanical sources, but plant materials often contain low concentrations of the desired flavour compound making extraction expensive. Also, the supply of raw materials is subject to seasonal and climatic variation, while in some cases socio-political instabilities in a producing region may threaten supply.

Many yeasts, molds and bacteria produce metabolites with flavour and fragrance attributes. In the United States, the Code of Federal Regulations states that products produced or modified by living cells or by their components, including enzymes, may be designated as "natural". Many flavours may therefore be produced by biotechnological means and marketed as natural in the U.S. The development of microbial fermentation technologies should increase the availability of many natural flavours, and thereby assure uniform quality and constant supply.

When methylotrophic yeasts of the genera Pichia, Torulopsis, Candida and Hansenula are grown using methanol as the sole source of carbon, subcellular vesicles known as peroxisomes are formed. These microbodies are the location of the enzyme alcohol oxidase, the first enzyme in the dissimilatory pathway that enables the organism to use methanol as the sole carbon source for growth. The enzymes of this pathway (shown below) have been purified and studied in detail by a number of workers.

sume (H. Sahm and F. Wagner, Eur. J. Biochem 36, 250, 1973).

Alcohol oxidase is of particular interest as a biotechnological tool because it is relatively nonspecific and because it is stable over a useful range of reaction conditions. A number of potential uses have been suggested for alcohol oxidase. These include use of the enzyme in a quantitative assay for alcohol, as an oxygen scavenger, for sterilization (through the release of formaldehyde) of heat- or radiation-sensitive materials, for the production of flavouring compounds (Alcohol oxidase product brochure, Provesta Corp., Bartlesville, Okla.), and as part of an ethanol recovery system (M. Kierstan, Biotechnol. Bioeng. 24, 2275, 1982). All of these applications have made use of cell-free extracts of varying purity as a source of alcohol oxidase. Other workers have succeeded in using both free and immobilized whole cells of *Hansenula polymorpha* for the production of formaldehyde from methanol (J. Baratti et al, Biotechnol. Bioeng, 20, 333, 1978; R. Couderc and J. Barati, Biotechnol. Bioeng. 22, 1155, 1980).

We have found whole cells of *Pichia pastoris* can be used with advantage in place of purified alcohol oxidase for the production of flavour aldehydes. Whole cells have a number of advantages over cell-free enzymes. Intracellular enzymes are protected from changes in conditions such as pH and ionic strength which may occur in the reaction vessel. As well, essential cofactors and coenzymes (such as FAD and catalase in the case of alcohol oxidase) are "co-immobilized" with the enzyme of interest, facilitating multistep reaction mechanisms. In this invention, a model system for aldehyde production was developed, based on the conditions for optimum conversion of ethanol to acetaldehyde.

In the production of flavour aldehydes a major limitation is the problem of end-product inhibition. It is known (U.S. Pat. No. 4,481,292) that this problem can be partially alleviated by chelating the aldehyde with alkaline Tris buffer. However, we have found that this complexing process is limited by the release of H+ and a subsequent drop in pH. Lower pH results in decreased Tris-aldehyde binding and a return to toxic aldehyde effects. It has been found that the problems with using the Tris buffer can be avoided by using a dual buffering system. The function of the Tris remains to bind the aldehyde while the additional buffering agent maintains

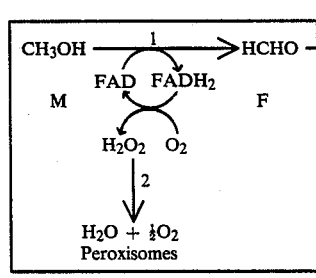
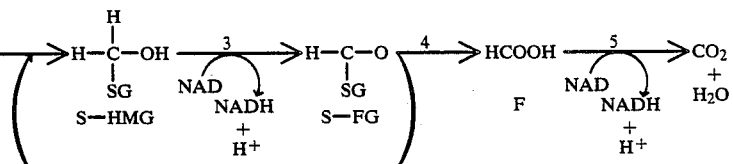

1: Alcohol oxidase
2: Catalase
3: Formaldehyde dehydrogenase
4: S—Formylglutathione-hydrolase
5: Formate dehydrogenase M: Methanol
F: Formaldehyde
S—HMG: S—Hydroxymethylglutathione
S—FG: S—Formylglutathione
G—SH: Reduced Glutathione
F': Formate Alcohol oxidase is under a repression/depression type of metabolic control system (H. Sahm, Adv. Biochem. Eng. 6, 77, 1973). Growth of the organism on soluble carbohydrate sources such as glucose prevents the formation of peroxisomes. During adaptation of the organism from growth on glucose to methanol, alcohol oxidase activity increases before growth is able to rethe pH close to 8. Alternately other amine buffers can be used which chelate aldehydes but maintain the pH near optimum levels.

U.S. Pat. No. 4,617,274 discloses a method of culturing yeast strains to produce a high cell density and the subsequent use of these cells for carrying out enzyme conversions. For example, methylotrophic yeasts can be used for the conversion of $C_3$-$C_6$ secondary alcohols to their corresponding methyl ketones using secondary alcohol dehydrogenase (SADH) (U.S. Pat. Nos. 4,241,184 and 4,266,034). Primary alcohols are, however, not oxidized by SADH.

U.S. Pat. No. 4,619,898 discloses a new alcohol oxidase isolated from Pichia-type organisms, which can be used in the production of aldehydes and hydrogen peroxide. The advantage of using a whole cell system over the purified enzyme has already been discussed.

SUMMARY OF THE INVENTION

According to the present invention, there is provided a process of oxidizing primary alcohols to aldehydes comprising:

(a) providing living whole cells of methylotrophic yeasts containing an active alcohol oxidase system in a buffer which is capable of forming a complex with the aldehyde product while maintaining the pH so that the aldehyde is not released from said complex;

(b) incubating the cells with the primary alcohol substrate in oxygen rich gas to facilitate the alcohol to aldehyde oxidation, the aldehyde forming a complex with the buffer, (c) reducing the pH to release the aldehyde from said complex; and (d) recovering the aldehyde.

Further according to the present invention the primary alcohols preferably are selected from the group consisting of: ethanol, propanol, butanol, isobutanol, pentanol, isoamylalcohol, 2-methyl butanol, hexanol and benzyl alcohol.

In a preferred embodiment of the present invention, the methylotrophic yeast is *Pichia pastoris* ATCC 28485 or a strain having the identifying characteristics thereof.

In the present invention the amine buffer is selected from the group consisting of: Tris [(hydroxy methyl) aminomethane]; Bicine [N,N-bis (2-hydroxyethyl)glycine]; Bis Tris Propane [1,2-bis tris hydroxymethylmethylamino propane]; Dipso [3-N,N-bis(2-hydroxyethyl)amino-2-hydroxypropanesulfonic acid]; 2-amino-2-methyl-1,3-propanediol; Tricine [N-tris hydroxymethyl methylglycine]; Tris-borate, Tris-barbital and Tris-phosphate.

BRIEF DESCRIPTION OF THE DRAWINGS

In the drawings which illustrate embodiments of the invention.

DETAILED DESCRIPTION

Figure 1:
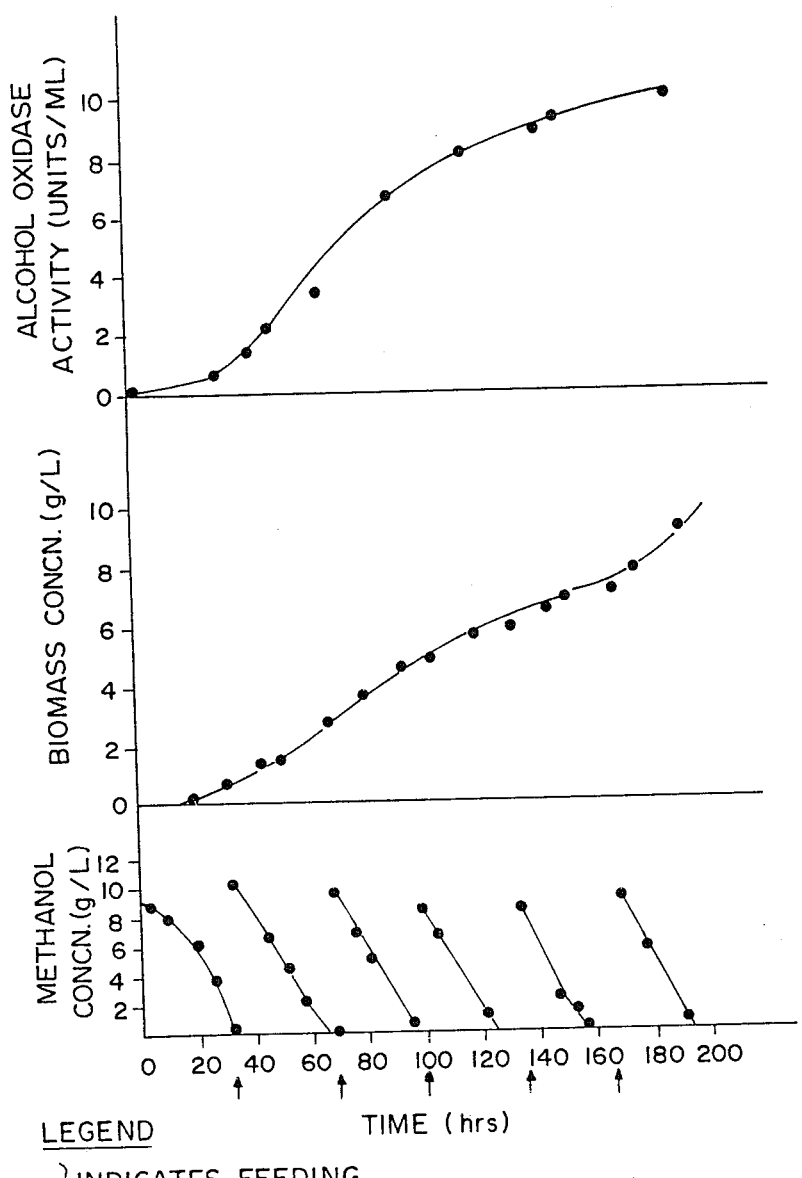
FIG. 1 shows a typical fed-bach fermentation of *P. pastoris* grown on methanol.

This invention relates to a method for using non-growing, metabolically active methylotrophic yeasts for the conversion of natural source alcohols to natural flavour aldehydes.

Methylotrophic yeasts from the four genera Pichia, Hansenula, Candida and Torulopsis were screened for their ability to produce acetaldehyde from ethanol. Of these, *P. pastoris* and *H. polymorpha* were similar in the specific rate and in the total amount of acetaldehyde produced. These two organisms were superior to all other species and were less susceptible to end product inhibition. Although *P. pastoris* was used to develop a model system for the conversion of ethanol to acetaldehyde, yeasts of the species *H. polymorpha* could also be used equally effectively. However other methylotrophic species, such as Candida and Torulopsis, would be operative.

The initial step in this process is to obtain metabolically active methylotrophic yeasts. Although many carbon sources, for example glucose, ethanol and methanol could be used for the production of biomass only growth on methanol resulted in derepression of alcohol oxidase synthesis. Biomass concentration could be increased by supplementing methanol with yeast extract (0.5 to 10.0 g/L) or with yeast extract (2-5 g/L) and glucose (5 g/L). However, except at low concentrations of yeast extract (0.5-1.0 g/L), there was a reduction in specific alcohol oxidase activity.

Other feeding regimes, fed-batch and continuous feeding were experimented with and found to increase biomass production and alcohol oxidase activity.

Although a number of methods could be used for the initial growth of *P. pastoris* (for example U.S. Pat. No. 4,617,274) the preferred method of this invention produces cultures that consistently have high uniform levels of alcohol oxidase activity.

In the conversion reaction a model system was developed using ethanol as the substrate. However, any other primary alcohol $C_2$-$C_7$ can be used in this process for the production of the corresponding aldehyde; for example, propanol, butanol, isobutanol, pentanol, isoamyl alcohol, 2-methyl butanol, haxanol and benzyl alcohol.

In the development of the model system reaction temperatures ranging from 7° C. to 40° C. were tested, and about 30° C. was found to be the preferred temperature. Between 5 g/L and 100 g/L of the substrate ethanol was tested in the conversion reaction. Good results were obtained from 40 g/L to 100 g/L; however, 50 g/L was chosen as the optimal substrate concentration.

The alcohol to aldehyde conversions can be carried out in a continuous system or in a batch conversion with the option of recycling the cells and the buffer. In a single batch conversion the reaction was allowed to proceed for 12 hours. When the cells were recycled in a batch conversion, the reaction was allowed to proceed for 5-6 hours before the cells were recycled.

As acetaldehyde accumulates end product inhibition is observed. This can be alleviated by the addition of a Tris buffer which chelates the aldehyde. Tris buffers with increasing molarity (0.2M to 1M) at pH 8.0 were tested and a Tris buffer molarity of 0.5M was chosen for subsequent tests.

The acetaldehyde forms a Schiff base with an amine group on the Tris molecule. This binding releases $H^+$ cations, which results in a concurrent drop in pH. This reduction in pH reduces the reaction rate and limits the vaibility of the biocatalyst. Therefore, other buffers were examined which could bind the acetaldehyde without causing a drop in pH. Two types of buffering systems were found to be of particular interest. The first was a dual buffer system such as Tris-borate, Tris-barbital and Tris-phosphate. It would be obvious to those skilled in the art that other dual buffering systems would work so long as the aldehyde is bound, the pH is maintained at about 7 to 10 and of course the buffer does not inactivate the alcohol oxidase. The second type of buffers found useful were other amine buffers such as: Bicine, Bis Tris, Dipso, 2-amino-2-methyl-1,3-propanediol and Tricine. Again, other amine buffers would work provided that the above listed criteria is met. Details of buffers found advantageous are given in Table VIII.

With the Tris buffer a molarity of 0.5M to 1.0M was optimal. With these other amine buffers the molarity used may range from about 0.5M to about 1.0M. The dual buffer had the following molarity: 0.5M Tris-0.15M borate buffer, 0.5M Tris-0.2 phosphate buffer, and 0.5M Tris-0.05M barbital buffer.

It has been found that these buffers can be reused. After the alcohol to aldehyde conversion is completed, the pH of the buffer is raised to release the bound aldehyde. Once the aldehyde has been recovered the pH of the buffer can be restored and the buffer reused in further conversions.

In the following examples the pH of the buffer was raised by the addition of a solution of HCl. It would be obvious to use solutions of other acids to raise the pH. The aldehyde was recovered with low temperature distillation; however it would be within the scope of this invention to use other known methods of recovering the aldehyde product.

As it will be further demonstrated in the following examples, the alcohol to aldehyde conversion can be accomplished using free cells or immobilized cells. A recycling regime of both the immobilized cells and the free cells have been found to be more productive than a single batch conversion.

The invention is illustrated further by the following examples which, however, are not to be taken as limiting in any respect.

EXAMPLE 1

Biomass Production and Specific Alcohol Oxidase Activity (a) Culture Media and Analyses

*P. pastoris* was obtained from the American Type Culture Collection (ATCC 28485). The medium used for maintenance and growth of the organism is shown in Table 1. If the concentration of carbon source was greater than 10 g/L, the concentration of ammonium sulfate was increased such that a constant C-N ratio was maintained. A vitamin solution (J. P. van der Walt and E. A. van Kerken, Antonie van Leeuwenhoek 27, 81, 1961) (2 mL/L) and methanol (10 g/L unless otherwise indicated) were added to the medium after it was autoclaved and cooled.

TABLE I

Medium used for growth of maintenance cultures, inoculum cultures and fermenter cultures of *P. pastoris*.*

| Compound | Maintenance | Inoculum | Fermenter |
|---|---|---|---|
| KH$_2$PO$_4$ | 2.6 | 0 | 0 |
| K$_2$HPO$_4$ | 3.2 | 17.4 | 1.74 |
| Citric acid | 0 | 6.95 | 0.695 |
| (NH$_4$)$_2$SO$_4$ | 1.5 | 3.0 | 3.0 |
| MgSO$_4$.7H$_2$O | 0.3 | 0.3 | 0.3 |
| FeSO$_4$.7H$_2$O | 1 × 10$^{-3}$ | 1 × 10$^{-3}$ | 1 × 10$^{-3}$ |
| CuSO$_4$.5H$_2$O | 5 × 10$^{-6}$ | 5 × 10$^{-6}$ | 5 × 10$^{-6}$ |
| H$_3$BO$_3$ | 1 × 10$^{-5}$ | 1 × 10$^{-5}$ | 1 × 10$^{-5}$ |
| MnSO$_4$.H$_2$O | 1 × 10$^{-5}$ | 1 × 10$^{-5}$ | 1 × 10$^{-5}$ |
| ZnSO$_4$.7H$_2$O | 7 × 10$^{-5}$ | 7 × 10$^{-}$ | 7 × 10$^{-5}$ |
| NaMoO$_4$.2H$_2$O | 1 × 10$^{-5}$ | 1 × 10$^{-5}$ | 1 × 10$^{-5}$ |

*All quantities in g/L. Methanol (10 g/L unless otherwise indicated) used as carbon source.

Methanol concentration in the fermentor was monitored using a Hewlett-Packard Model 5790A gas chromatograph equipped with a Chromasorb (TM) 101 column. The carrier gas used was helium, and the column was maintained at 180° C. To determine biomass concentration, 10-mL samples of culture broth were filtered onto preweighed filter disks (0.45 μm pore size, Millipore, Bedford MA), washed, and dried overnight at 105° C. Biomass dry weight was determined by difference. A second 10-mL sample was removed from the culture broth to determine alcohol oxidase activity. The sample was centrifuged (4000 g, 15 min), and the pellet was washed with 10 mL citrate-phosphate buffer (K$_2$HPO$_4$, 0.25M; citric acid, 0.02M; MgSO$_4$.7H$_2$O, 0.12 mM; pH 5.8). The biomass was then recentrifuged and resuspended in 0.5M Tris buffer, pH 8. Ethanol was used as a substrate to determine alcohol oxidase activity in the presence of excess oxygen at 30° C. Samples were removed from the reaction vessel, centrifuged to remove biomass, and diluted with an equal volume of 1.55% (v/v) HCl. This step was necessary to reduce the pH to ~6 and liberate the aldehyde product from the formed Tris-aldehyde complex. The concentrations of ethanol and acetaldehyde in the reaction vessel were monitored using a Shimadzu (TM) GC-9A gas chromatograph equipped with a Supelcowax (TM) 10 fused silica capillary column. Column temperature was controlled at 60° C., and helium was used as the carrier gas. One unit of alcohol oxidase activity was defined as 1 μmol acetaldehyde produced/mL min in the reaction flask. Dividing this activity by the biomass dry weight yielded a value for specific alcohol oxidase activity (units/g dry weight of biomass).

(b) Batch Fermentation

In batch fermentations carried out at methanol concentrations that varied over the range 10–50 g/L (Table II), only those cultures with initial methanol concentrations of 10 and 20 g/L were able to completely metabolize the substrate. Biomass concentrations produced were low (<2.5 g/L) and the biomass yield coefficient, Y$_{x/x}$ (g biomass/g methanol used) decreased from a maximum of 0.18 at the lowest concentration of methanol used to a minimum value of 0.06 at the highest methanol concentration (50 g/L).

Methanol concentrations in excess of 20 g/L not only caused decreased biomass production but also resulted in a reduction of the specific alcohol oxidase activity of the cell. The disappearance of peroxisomes and concurrent reduction in alcohol oxidase activity in the presence of excessive amounts of substrate has been previously reported for Hansenula (J. P. van Dijken et al, Arch. Microbiol. 111, 137, 1976).

TABLE II

Effect of initial methanol concentration on growth and alcohol oxidase activity of P. pastoris in batch culture

| Methanol concentration (g/L) | | Final biomass concentration (g/L) | Biomass yield coefficient ($Y_{x/x}$) | Biomass productivity (g/L/day) | Specific alcohol oxidase activity (units/g) |
|---|---|---|---|---|---|
| Initial | Consumed | | | | |
| 10 | 10 | 1.8 | 0.18 | 0.40 | 2045 |
| 20 | 20 | 2.2 | 0.11 | 0.40 | 2300 |
| 30 | 23 | 2.0 | 0.09 | 0.27 | 2125 |
| 40 | 28 | 1.9 | 0.07 | 0.25 | 1820 |
| 50 | 34 | 1.9 | 0.06 | 0.25 | 1475 |

Under methanol limitation, a condition that favours full depression of the alcohol oxidase enzyme system, the specific activity of the Pichia biomass did not vary appreciably (Table II). For this reason the object of the fermentation became to increase biomass productivity. This was attempted by adding yeast extract alone or in combination with a second carbon source, glucose. Addition of yeast extract alone to methanol-based growth media resulted in an increase in biomass production and in specific alcohol oxidase activity (Table III). The limited depression of alcohol oxidase activity observed reflected the high concentration of methanol that remained at the time the cultures were assayed (J. P. van Dijken et al, op. cit.). A yeast extract concentration of 1 g/L resulted in the maximum specific activity observed (1290 units/g biomass). Higher concentrations of yeast extract resulted in a reduction in activity. This was likely due to a repressive effect on alcohol oxidase synthesis caused by the soluble carbohydrate content of the yeast extract.

TABLE III

Effect of yeast extract addition on biomass production and specific alcohol oxidase activity in P. pastoris cultures grown for 48 h

| Yeast extract concentration (g/L) | Biomass concentration (g/L) | Specific alcohol oxidase activity (units/g biomass) |
|---|---|---|
| 0 | 0.79 | 1100 |
| 0.5 | 0.93 | 1160 |
| 1.0 | 1.11 | 1290 |
| 5.0 | 1.67 | 1210 |
| 10.0 | 2.22 | 1180 |

The addition of a combination of glucose and yeast extract (5 g/L of each) to the growth medium resulted in the production of 3 g/L of P. pastoris biomass, a 66% increase over that observed in control flasks (Table IV). Delayed addition of methanol did not serve to enhance the growth rate during the initial phase of growth because methanol was not used until all of the soluble carbohydrate had been consumed. Although these additions increased the yield of biomass, the diauxic growth experienced by P. pastoris caused a 36% reduction in the specific alcohol oxidase activity of the cells. Our work with P. pastoris contrasts that reported for H. polymorpha, where soluble carbon sources were used to enhance growth with no loss of alcohol oxidase activity (L. Eggeling and H. Sahm, Microbiol. 127, 119, 1980).

TABLE IV

Effect of varied yeast extract and delayed methanol addition on growth and alcohol oxidase activity of P. pastoris grown in presence of glucose.*

| Medium component (g/L) | | | Biomass concentration (g/L) | Alcohol oxidase activity (units/L) | Specific activity (units/g biomass) |
|---|---|---|---|---|---|
| Yeast extract | Glucose | MeOH | | | |
| 5 | 5 | 10 (I) | 3.00 | 3910 | 1305 |
|  |  | 10 (D) | 3.05 | 4580 | 1500 |
| 2 | 5 | 10 (I) | 2.60 | 4200 | 1615 |
|  |  | 10 (D) | 2.25 | 4150 | 1845 |
| 0 | 0 | 10 (I) | 1.80 | 3680 | 2045 |

*Letters in parentheses signify that methanol was added either initially (I) or after a 48 h delay (D)

(c) Fed Batch and Continuous Cultivation

A typical fed-batch fermentation profile is illustrated in FIG. 1. As biomass accumulated over the time course of the fermentation, the rate of methanol uptake increased slowly from approximately 1.8 g/L/h during the initial batch growth phase to approximately 2.5 g/L/h after five feeding cycles. The rate of increase in biomass concentration and alcohol oxidase activity were relatively constant over the course of the fermentation. By using an intermittant methanol feeding regime, the difficulties associated with methanol inhibition in batch cultures were avoided. As a result, the biomass concentration was increased to approximately 10 g/L while the overall biomass productivity increased by a factor of 3.5 over the productivity achieved in batch cultivations (Table V).

TABLE V

Effect of fed-batch fermentation on P. pastoris biomass yield and alcohol oxidase activity

| Initial methanol concentration (g/L) | Total added methanol (g/L) | Final biomass concentration (g/L) | Overall biomass productivity (g/L/day) | $Y_{x/x}$ | Alcohol oxidase activity (units/mL) |
|---|---|---|---|---|---|
| 10 | 40 | 5.8 | 1.37 | 0.15 | 7.7 |
| 10 | 50 | 8.0 | 1.45 | 0.16 | 8.4 |
| 10 | 60 | 9.9 | 1.41 | 0.16 | 9.7 |

Continued feeding such that the total concentration of methanol added was over 60 g/L did not result in further increases in the concentration of biomass produced. Biomass concentrations of up to 26 g/L and biomass productivities of up to 2.5 g/L/d were achieved in experiments during which methanol was added continuously after one batch growth cycle (Table VI). A hybrid feeding regime, which involved a fed-batch mode of operation for eight feeding cycles followed by a continuous feeding period, did not result in further improvements in biomass productivity.

TABLE VI

Effect of two types of continuous feeding on biomass concentration, biomass productivity, and yield coefficient during fermentations with *P. pastoris*

| | Biomass Concentration | | Biomass productivity | |
|---|---|---|---|---|
| | Initial | Final | (g/L/day) | $Y_{x/x}$ |
| Continuous feed after 1 batch cycle | 0.5 | 26.1 | 2.45 | 0.17 |
| Continuous feed after 8 batch cycles | 10.6 | 17.5 | 1.02 | 0.08 |

From the preceding results it can be concluded that fed-batch or continuous feeding of methanol increased the biomass productivity and final biomass concentration over that which could be achieved in batch cultivation.

EXAMPLE 2

Conversion Assay - Ethanol to Acetaldehyde: A Model System

The methylotrophic yeast *P. pastoris* (ATCC 28485) was grown in a simple vitamin-mineral salts medium containing: $KH_2PO_4$, 2.6 g; $K_2HPO_4$, 0.37 g; $(NH_4)_2SO_4$, 1.5 g; $MgSO_4.7H_2O$, 0.3 g; $FeSO_4.7H_2O$, 1 mg; $ZnSO_4.7H_2O$, 70 μg; $Na_2MoO_4.2H_2O$, 10 μg; $MnSO_4.H_2O$, 10 μg; $H_3BO_3$, 10 μg; and $CuSO_4.5H_2O$, 5 μg; per liter of $H_2O$. After the medium had been autoclaved and cooled, filter-sterilized methanol (1% w/v) and 2 ml of a sterile vitamin solution (J. P. van der Walt and A.E. van Kerken, 1961, op.cit.) were added.

A 4% (v/v) inoculum of *P. pastoris* was used and the culture incubated at 30° C. with rotary shaking at 200 rpm. Cultures were harvested by centrifugation after 72 h of growth. The cells were washed once with 20 mM phosphate buffer, pH 6, and resuspended to a density of 5 g/L in 0.5M Tris-HCl buffer, pH 8. They were stored at 4° C. and used within 2 weeks with no loss of activity.

Ethanol to acetaldehyde conversions were carried out in 160 ml serum vials, containing 25 ml of cell suspension. The vials were flushed with $O_2$, injected with the ethanol substrate (5% w/v), and sealed to prevent loss of reaction product. The vials were pressurized with $O_2$ to 100 kPa. Vials were incubated at 30° C. in an incubator shaker (200 rpm), and were recharged with $O_2$ as required. Samples were removed, centrifuged (15000 g, 2 min), and diluted 1:1 with a 1.55% (v/v) HCl solution. This procedure reduced the pH to approximately 6 and released the acetaldehyde from the Tris-aldehyde complex formed at pH 8 (U.S. Pat. No. 4,481,292). Ethanol and acetaldehyde concentrations were quantified on a Shimadzu GC9A gas chromatograph, equipped with a FID detector, and a DBWAX (TM)-30m fused silica capillary column (J & W Scientific Inc., Rancho Cordova, Calif.). Column temperature was controlled at 100° C., and helium was used as the carrier gas. Specific activity calculations were based on the amount of acetaldehyde produced during the first hour of reaction per g of cells.

Figure 2:
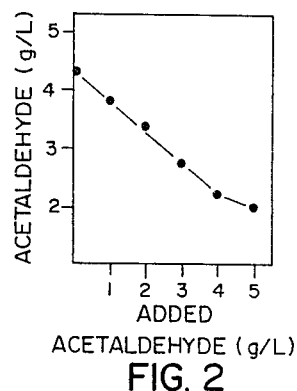
FIG. 2 demonstrates the effect of exogenously added acetaldehyde on the conversion of ethanol to acetaldehyde at 4 hours.
Figure 3:
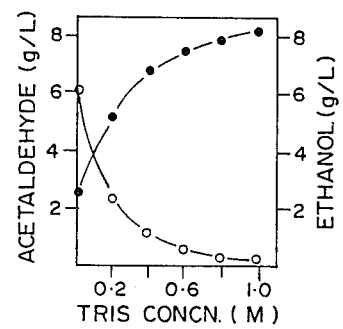
FIG. 3 depicts the effect of Tris buffer molarity on the conversion of ethanol to acetaldehyde at 4 hours.

Since acetaldehyde is extremely volatile with a boiling point of 21° C., a closed-batch process was examined in order to retain and quantitate the product. Acetaldehyde in a closed system was found to cause end-product inhibition when it was exogenously added at concentrations up to 5 g/L (FIG. 2). Tris buffer at a pH value greater than 7 is known to readily chelate acetaldehyde in a 1:1 molar ratio. When the ethanol to acetaldehyde conversion was run in Tris buffers of increasing molarity, at pH 8, it was found that end-product inhibition was increasingly alleviated (FIG. 3). A Tris buffer molarity of 0.5 was chosen for subsequent tests.

Figure 4:
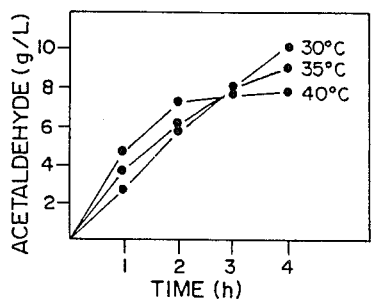
FIG. 4 demonstrates acetaldehyde production at 30°, 35° and 40° C.

Purified alcohol oxidase from *P. pastoris* has been reported to have maximum activity at 37° C. and pH 7.5 (C. Couderc and J. Baratti, Agric. Biol. Chem. 44, 2279, 1980). In our whole-cell studies the initial acetaldehyde production rate was maximum at 40° C.; however, alcohol oxidase activity appeared unstable at this temperature and rapidly levelled off. When the conversion was run at 30° C. a constant rate of relatively high activity was maintained (FIG. 4). Conversions conducted at pH 4 to 9 exhibited only slight variation in enzyme activity or product yield. It is assumed that a whole-cell system protects the intracellular enzymes from pH extremes in the external environment.

The effect of substrate concentration was investigated during a 12 h conversion reaction. Ethanol concentrations below 10 g/L were found to be limiting, while maximum acetaldehyde production occurred within an ethanol range of 50 to 75 g/L. Inhibition was noted at ethanol levels greater than 75 g/L.

Figure 5:
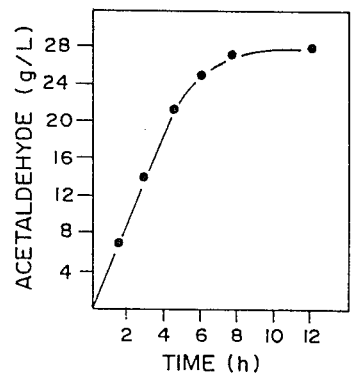
FIG. 5 demonstrates a typical model system of ethanol to acetaldehyde conversion.

The preferred conditions found for optimum acetaldehyde production were a biomass concentration of 5 g/L suspended in 0.5M Tris-HCl buffer, pH 8, 30° C., unlimiting $O_2$ at positive pressure, and a substrate ethanol level of 50 g/L. FIG. 5 illustrates the time course of an ethanol to acetaldehyde conversion under these conditions. In this typical example, the specific rate of acetaldehyde production during the first 4.5 h was 1.07 g/g of cells/h, at a conversion efficiency (carbon recovery) of greater than 97%. The rate of conversion remained steady until the chelating capacity of the 0.5M Tris-HCl buffer (22 g/L acetaldehyde) was met. End production inhibition was then experienced and maximum yields of 27-30 g/L were obtained.

EXAMPLE 3

Conversion of other Alcohols to Flavour Aldehydes

The model system developed for the batch conversion of ethanol to acetaldehyde has been successfully applied to the production of other flavour aldehydes (Table VII). For alcohols that have low solubility in water, conversions were tested at their solubility level. Higher product accumulation may have occurred by maintaining the substrate at the saturation level by subsequent substrate addition.

TABLE VII

Bioconversion of alcohols to flavour aldehydes

| Substrate | Product | Initial Substrate Conc. (g/L) | Final Product Conc. (g/L)[a] |
|---|---|---|---|
| Propanol | propionaldehyde | 50 | 25.4 |
| Butanol | butyraldehyde | 50 | 25.1 |
| Isobutanol | isobutyraldehyde | 50 | 16.5 |
| Benzyl alcohol | benzaldehyde | 20 | 5.9 |
| Pentanol[b] | valeraldehyde | 20 | 18.7 |
| Isoamyl alcohol[b] | isovaleraldehyde | 20 | 6.2 |
| 2-Methyl butanol[b] | 2-methyl butyraldehyde | 20 | 6.7 |
| Hexanol[b] | hexanal | 5 | 5.0 |

[a]12-h batch conversions, conducted under positive $O_2$ pressure, 30° C., 0.5 M Tris HCl, pH 8.0, methanol grown *P. pastoris* cells, 5 g/L.
[b]All substrates were at or near their saturation levels.

EXAMPLE 4

Bioconversion conducted in other amine buffers

In the preceding examples Tris buffer (0.5M Tris HCl, pH 8.0) was used as the reaction medium because of its ability to bind acetaldehyde in stoichiometric quantities. The use of the Tris buffer limits the exposure of the P. pastoris cells to the damaging effect of the end product and allows for increased production of acetaldehyde. Acetaldehyde forms a Schiff base with an amine group on the Tris molecule. This binding releases $H^+$ cations however, resulting in a concurrent drop in pH. This reduction in pH reduces the reaction rate and limits the viability of the biocatalyst.

A dual buffer system (at 0.5M Tris, plus sufficient second buffer to maintain the pH above 7.0) has been used to carry out the alcohol to aldehyde conversion. The Tris functions to bind the aldehyde as before whereas the additional buffering agent maintain the pH close to 8.0 (Table VIII). Alternatively, other amine buffers (0.5M) can be used which chelate the aldehydes without the concurrent drop in pH as exhibited with Tris buffer (Table VIII). Accordingly, these buffers are an improvement over Tris in that a dual buffering system is not required. Further, it was found that aldehyde production in the presence of 2-amino-2-methyl-1,3-propanediol buffer was found to be 25% greater than that measured in Tris buffer.

TABLE VIII

Comparison of ethanol to acetaldehyde conversion by P. pastoris in different amine buffers and dual buffer systems

| Buffer | Acetaldehyde produced (g/L) at | | | | pH 24 h |
|---|---|---|---|---|---|
| | 2 h | 4 h | 6 h | 24 h | 24 h |
| Tris (pH 8) [Tris(hydroxymethyl)amino-methane] | 5.5 | 11.57 | 17.0 | 27.3 | 5.5 |
| Bicine (pH 8) [N,N—bis(2-hydroxyethyl) glycine] | 6.0 | 10.7 | 14.8 | 25.5 | 7.6 |
| Bis Tris Propane (pH 8) [1,3-bis tris hydroxymethyl-methylamino propane] | 6.98 | 9.8 | 15.1 | 30.8 | 7.2 |
| Dipso (pH 8) 3-N,N—bis(2-hydroxyethyl) amino-2-hydroxypropane-sulfonic acid] | 7.13 | 12.2 | 17.0 | 26.1 | 7.2 |
| 2-amino-2-methyl-1,3-propanediol (pH 9) | 8.2 | 13.77 | 19.8 | 35.5 | 7.2 |
| Tricine (pH 9) [N—Tris(hydroxymethyl)methyl-glycine] | 7.26 | 10.9 | 15.0 | 30.9 | 7.5 |
| Tris-borate (pH 8) | 4.7 | 10.1 | 15.5 | 28.7 | 7.1 |
| Tris-barbital (pH 8) | 5.2 | 11.1 | 17.0 | 27.2 | 7.0 |
| Tris-phosphate (pH 8) | 5.0 | 10.2 | 15.7 | 26.7 | 7.3 |

Aldehydes produced by our model system of Example 2 have been found to act as catabolite inactivators. For example, free acetaldehyde either causes the conformational change of alcohol oxidase making it susceptible to attack by proteases, or acetaldehyde activates dormant proteases. The problem was circumvented by recycling cells in a multiple batch process prior to the accumulation of free acetaldehyde. When cell recycle experiments (6 h conversion periods) were carried out in Tris buffer containing 5 g/L of cells, acetaldehyde production dropped off after the second conversion, with total acetaldehyde production after 3 conversion cycles of only 37 g/L. Total acetaldehyde production was greatly improved when the dual buffering systems were used. For example, in the Tris-borate buffer five conversion cycles were possible with total acetaldehyde production of 71 g/L. Similarly, 70.4 g/L of acetaldehyde were produced after four conversion cycles in the 2-amino-2-methyl-1,3-propanediol buffer (Table IX).

TABLE IX

Comparison of acetaldehyde production in batch conversions with P. pastoris cell recycle in amine buffers and dual-buffer systems

| Buffer* | Cell recycle (6 h conversions) | | | | | Total Acetaldehyde (g/L) |
|---|---|---|---|---|---|---|
| | 1 | 2 | 3 | 4 | 5 | |
| Tris | 16.8 | 14.4 | 3.0 | 2.95 | 0 | 37.2 |
| Bicine | 12.9 | 10.7 | 9.9 | 4.8 | 4.2 | 42.5 |
| Bis Tris | 13.5 | 12.0 | 7.5 | 4.3 | 0 | 37.3 |
| Dipso | 13.4 | 11.4 | 9.1 | 4.4 | 4.3 | 42.6 |
| 2-amino-2-methyl-1,3-propanediol | 21.3 | 21.0 | 18.9 | 8.9 | 2.0 | 72.1 |
| Tricine | 11.4 | 10.7 | 11.0 | 9.1 | 8.8 | 51.0 |
| Tris-Borate | 15.3 | 19.9 | 16.8 | 13.4 | 5.3 | 70.7 |
| Tris-Barbital | 10.8 | 12.8 | 13.1 | 10.2 | 6.6 | 53.5 |
| Tris-Phosphate | 15.4 | 16.5 | 16.3 | 10.2 | 3.6 | 62.0 |

*Initial pH as shown in TABLE VIII

Accordingly, it is our proposal to carry out either continuous conversions with product stripping, or batch conversions with cell recycle in any of the dual buffering systems described, or in the single buffer systems: Bicine buffer, Bis tris propane buffer, Dipso buffer, Tricine buffer, or 2-amino-2-methyl-1,3-propanediol buffer.

EXAMPLE 5

Immobilized P. pastoris cells for the conversion of ethanol to acetaldehyde

Washed P. pastoris biomass was suspended in a sodium alginate solution such that the final concentration of sodium alginate was 20 g/L. Biomass concentration in the alginate was varied. The suspension was thoroughly mixed and added dropwise through an 18 gauge needle to a stirred solution of $CaCl_2$ (40 g/L). The diameter of the beads generated was 2.7 mm.

The effect of biomass loading on the specific activity of immobilized P. pastoris was studied at a fixed concentration of alginate (20 g/L). Although the initial volumetric rate of acetaldehyde production increases with increasing biomass loading, the specific rate of acetaldehyde produced decreases. This indicates that, with increased biomass concentration, the catalytic capabilities of the immobilized cells were increasingly underutilized.

The alcohol oxidase activity of P. pastoris cells which had been immobilized and allowed to grow in calcium alginate beads was compared to that of freshly immobilized cells.

Yeast biomass which was immobilized at the lowest concentration showed the greatest increase in biomass concentration during the regrowth period. The final amount of biomass accumulated varied little (3.3–3.9 g/L), regardless of the initial biomass concentration immobilized. This indicates that there is an upper limit to the biomass concentration which can be reached inside a calcium alginate bead. This limit reflects the increasing importance of oxygen and nutrient diffusional limitations on the system as the concentration of biomass within the bead increases.

The catalytic activity of the immobilized cells was unchanged for beads formed with pre-grown biomass, or with biomass which was grown within the beads. As biomass concentration increases, the decrease in specific alcohol oxidase activity is again observed. Thus, there is no loss of activity which occurs as a result of the immobilization treatment. Since aseptic conditions must be maintained throughout the immobilization procedure, it is technically more difficult to grow the yeast inside the beads than it is to simply immobilize the desired concentration of cells. For a large-scale process, re-growth of cells in the immobilized beads is impractical.

Figure 6:
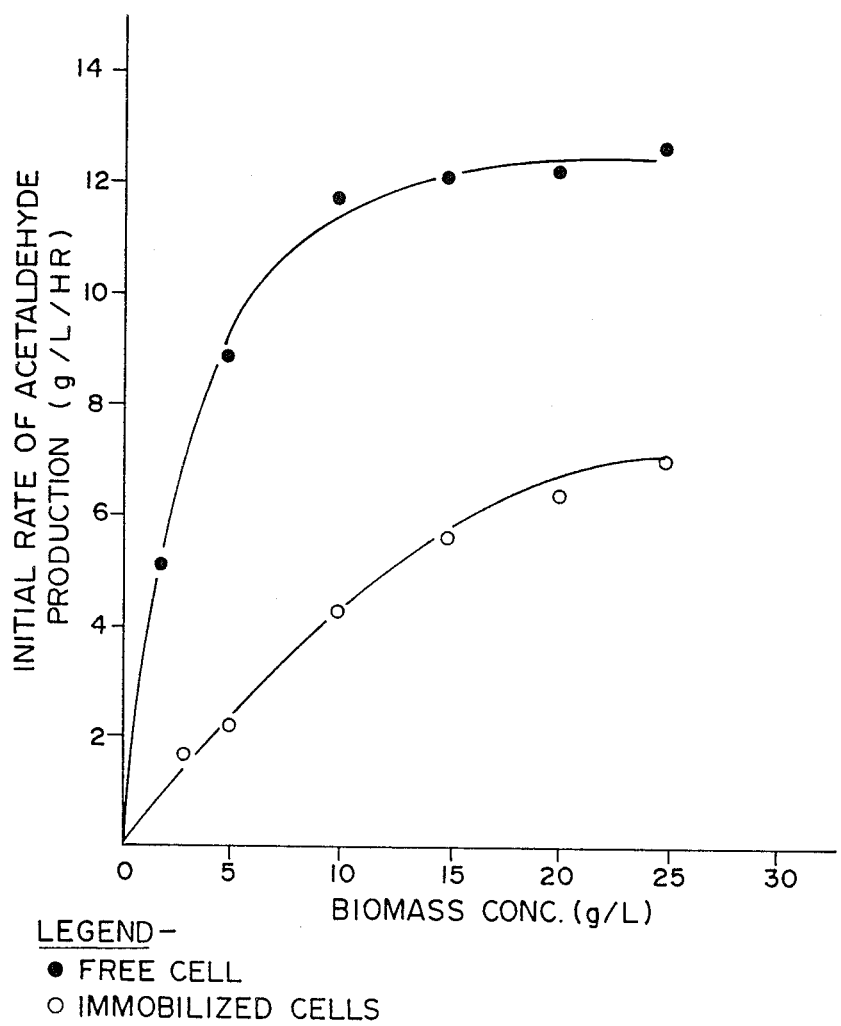
FIG. 6 compares the catalytic activity of free and immobilized cells at various conditions of biomass loading.

According to classical Michaelis-Menton enzyme kinetic theory, initial reaction rate should be linearly proportional to the initial concentration of biocatalyst. The linear relationship between reaction rate and biocatalyst concentration was found to hold for *P. pastoris* free cell concentrations of up to 0.5 g/L in the reaction flask (FIG. 6). Higher concentrations (up to 25 g/L) of biocatalyst resulted in a sharp flattening of the rate vs. biomass concentration curve (FIG. 6). When calcium alginate-immobilized cells of *P. pastoris* were used to catalyse the ethanol to acetaldehyde reaction, the linear relationship between reaction rate and biomass concentration held at higher levels of biocatalyst loading. This slower rate of decline of initial reaction rate can be explained by two factors. Firstly, since immobilized cells are less active as biocatalysts, the amount of acetaldehyde produced during the 1-hour test period was less for any given biomass concentration. As a result, end-product inhibition of the reaction by acetaldehyde was reduced as compared to the more active free cells. As well, it is likely that the rate of reaction is, to some extent, physically controlled in the immobilized system. It has been shown that in other calcium-alginate immobilized systems, diffusion of oxygen into the beads is restricted by the polymer matrix. Introduction of this external physical control reduces the dependence of reaction rate on catalyst concentration.

Figure 7:
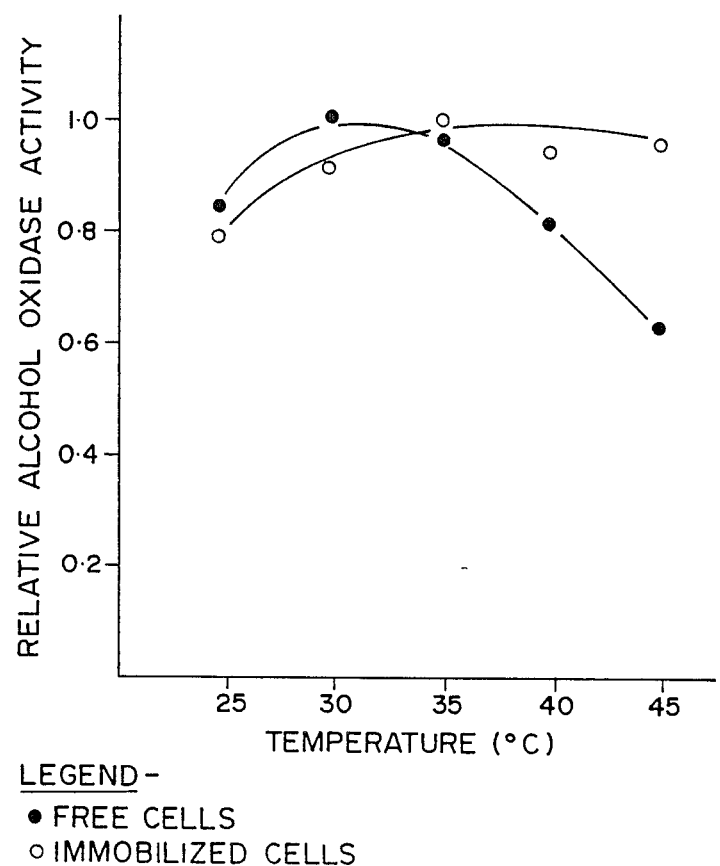
FIG. 7 shows that effect of temperature on alcohol oxidase activity of free and immobilized cells.

The temperature at which the conversion reaction was carried out had a pronounced effect on the activity of free cells of *P. pastoris* (FIG. 7). The optimum temperature for conversion was found to be approximately 30° C. When the temperature of the reaction vessel was increased beyond the optimum value, a rapid decline in activity was observed to the extent that at 45° C., only 60% of the control activity remained. *P. pastoris* cells immobilized in calcium alginate had a higher temperature optimum (35° C.), and showed little variation in activity when higher temperatures were used. This increased resistance to heat denaturation supports similar findings using *H. polymorpha* immobilized in polyacrylamide gels (R. Couderc and J. Baratti, Biotech. Bioeng. 22, 1155, 1980).

Attempts were made to use both free and immobilized *P. pastoris* cells for repeated batch conversion reactions. Immobilized cells retained much of their activity throughout repeated batch reactions at a variety of different incubation temperatures (Table X). By comparison, attempts to recycle free cells were largely unsuccessful. At 30° C., free cells lost 60% of their activity after one batch cycle, and 90% after two cycles.

TABLE X

Effect of temperature on alcohol oxidase activity during repeated batch reactions using immobilized *P. pastoris*

| Cycle Number | Specific Rate of Acetaldehyde Production (g AcH/g cells/h) | | |
|---|---|---|---|
| | 1 | 2 | 3 |
| Temp. (°C.) | | | |
| 25 | 2.12 | 1.69 | 1.08 |
| 30 | 2.16 | 1.78 | 1.45 |
| 35 | 2.00 | 1.49 | 0.81 |
| 40 | 1.92 | 1.32 | 0.67 |

Therefore, non-growing cells of *P. pastoris* can be used to catalyse the oxidation of ethanol to acetaldehyde. The temperature stability of the alcohol oxidase activity can be increased by cell entrapment in a calcium alginate matrix. Alcohol conversion rates are lower for immobilized *P. pastoris* cells, however the beads can be used repeatedly in batch reactors.

We claim:

1. A process of oxidizing primary $C_2$-$C_7$ alcohols to aldehydes comprising:
    (a) providing non-growing living whole cells of methylotrophic yeasts containing an active methanol-induced alcohol oxidase system in an alkaline buffer which is capable of forming a complex with the aldehyde product at high pH while maintaining the high pH so that the aldehyde is not released from said complex;
    (b) incubating the cells with the primary alcohol substrate in oxygen rich gas to facilitate the alcohol to aldehyde oxidation, the aldehyde forming a complex with the buffer,
    (c) reducing the pH to release the aldehyde from said complex; and
    (d) recovering the aldehyde.

2. The process of claim 1 wherein the buffer of step (a) is an amine buffer at about pH 7 to 10.

3. The process of claim 1 wherein the primary alcohols are selected from the group consisting of: ethanol, propanol, butanol, isobutanol, pentanol, isoamyl alcohol, 2-methyl butanol, hexanol, and benzyl alcohol.

4. The process of claim 1 wherein the methylotrophic yeasts are selected from the group consisting of: yeasts of the genera Pichia, Hansenula, Torulopsis and Candida.

5. The process of claim 2 wherein the yeasts of the genus Pichia is *P. pastoris*.

6. The process of claim 3 wherein the yeast is *P. pastoris* with the identifying characteristics of *P. pastoris* ATCC 28485.

7. The process of claim 1 wherein the methylotrophic yeasts are pregrown on methanol at a cumulative concentration of 10 g/L to 60 g/L.

8. The process of claim 7 wherein the mode of addition of methanol was selected from the group consisting of: batch, fed-batch, and continuous feeding.

9. The process of claim 8 wherein yeast extract was added in combination with the methanol in the batch feeding.

10. The process of claim 9 wherein the yeast extract was added at a concentration of about 0.5 g/L to 1.0 g/L.

11. The process of claim 3 wherein when the primary alcohol is selected from the group consisting of ethanol, propanol, butanol, benzyl alcohol and isobutanol, the concentration of substrate ranges from 20 g/L to 100 g/L, and when the primary alcohol is selected from the group consisting of pentanol, isoamylalcohol, 2-methyl butanol and hexanol, the concentration of substrate is at or near the saturation level, and may be maintained at the saturation level by subsequent substrate addition.

12. The process of claim 1 wherein in step (a) the cells are provided at a density of about 5 g/L in 0.5 to 1.0M buffer.

13. The process of claim 1 wherein in step (b) the incubation step occurs at about 30° C. in a incubator shaker (at about 200 rpm) and $O_2$ is added under positive pressure to maintain an oxygen rich environment.

14. The process of claim 2 wherein the amine buffer is selected from the group consisting of: tris(hydroxymethyl)amino-methane; N,N-bis 2-hydroxyethyl glycine; 1,3-bis tris hydroxymethylmethylamino propane; 3-N,N-bis(2-hydroxyethyl)amino-2-hydroxypropane sulfonic acid; 2-amino-2-methyl-1,3-propanediol; N-tris hydroxymethylmethyl glycine; Tris-borate; Tris-barbital and Tris-phosphate.

15. The process of claim 1 which further comprises recovering the cells following the incubation step (b) and recycling them for repeated use.

16. The process of claim 1 wherein the cells of step (a) are provided in an immobilizing matrix.

17. The process of claim 1 wherein the aldehyde is recovered by low temperature distillation.

18. The process of claim 1 wherein the pH is reduced to about pH 6 in step (c) by diluting 1:1 with a 1.55% (v/v) HCl solution.

19. The process of claim 1 which further comprises:
(e) recovering the buffer, and
(f) increasing the pH so that the buffer can be recycled to step (a).

20. A process of oxidizing primary alcohols to aldehydes comprising:
(a) growing cells of methylotrophic yeasts on methanol (10 g/L) to induce the production of alcohol oxidase at 30° C. with rotary shaking at 200 rpm;
(b) harvesting the cells after 72 hours of growth;
(c) resuspending the harvested cells in 0.5M amine buffer, pH 8-9 at a density of 5 g/L;
(d) incubating 25 mL of the resuspended cells, in 160 mL vials flushed with $O_2$, with the primary alcohol 5% w/v at 30° C. with rotary shaking at 200 rpm for 5-12 hours, the produced aldehyde forming a complex with the amine buffer;
(e) reducing the pH to about pH 6 to release the aldehyde from the complex by diluting 1:1 with a 1:55% (v/v) HCl solution; and
(f) recovering the aldehyde by low temperature distillation.

* * * * *